(12) United States Patent
Fox et al.

(10) Patent No.: US 8,184,769 B2
(45) Date of Patent: May 22, 2012

(54) METHOD AND APPARATUS TO FACILITATE USING MULTIPLE RADIATION-DETECTION VIEWS TO DIFFERENTIATE ONE MATERIAL FROM ANOTHER

(75) Inventors: Timothy R. Fox, Chicago, IL (US); Gongyin Chen, Henderson, NV (US); Kevin M. Holt, Chicago, IL (US); Paul J. Bjorkholm, Newport Beach, CA (US); David T. Nisius, Des Plaines, IL (US)

(73) Assignee: Varian Medical Systems, Inc., Palo Alto, CA (US)

( * ) Notice: Subject to any disclaimer, the term of this patent is extended or adjusted under 35 U.S.C. 154(b) by 149 days.

(21) Appl. No.: 12/479,376

(22) Filed: Jun. 5, 2009

(65) Prior Publication Data
US 2010/0310042 A1 Dec. 9, 2010

(51) Int. Cl.
*G01N 23/06* (2006.01)
(52) U.S. Cl. .......................... 378/53; 378/98.9
(58) Field of Classification Search .............. 378/53, 378/92, 98.8, 98.9; 382/132
See application file for complete search history.

(56) References Cited

U.S. PATENT DOCUMENTS

| | | | |
|---|---|---|---|
| 4,511,799 A | 4/1985 | Bjorkholm | |
| 5,319,547 A | 6/1994 | Krug et al. | |
| 5,481,584 A | 1/1996 | Tang et al. | |
| 5,524,133 A | 6/1996 | Neale et al. | |
| 5,548,123 A | 8/1996 | Perez-Mendez et al. | |
| 5,917,880 A | 6/1999 | Bjorkholm | |
| 6,069,936 A | 5/2000 | Bjorkholm | |
| 7,257,188 B2 | 8/2007 | Bjorkholm | |
| 7,330,532 B2 * | 2/2008 | Winsor | 378/98.9 |
| 7,724,865 B2 * | 5/2010 | Wu et al. | 378/5 |
| 7,869,559 B2 * | 1/2011 | Ikhlef et al. | 378/5 |
| 2007/0183568 A1 | 8/2007 | Kang et al. | |
| 2009/0129544 A1 | 5/2009 | Chen et al. | |

OTHER PUBLICATIONS

EP Search Report from related application No. EP10164833.5; Oct. 19, 2010; 5 pages.
Maitrejean et al., "Multi-Energy Method: A New Approach for Measuring X-Ray Transmission as Function of Energy with a Bremsstrahlung Source. Application for Heavy Element Identification," Proceedings for the International Society for Optical Engineering; vol. 3446; pp. 114-133; Jul. 22, 1998.
Rebuffel et al., "Dual-Energy X-Ray Imaging: Benefits and Limits," Insight (Non-Destructive Testing and Condition Monitoring, British Institute of Non-Destructive Testing; vol. 40, Issue 10; pp. 589-594; Oct. 1, 2007.
Extended European Search Report for related EP Application No. 10164828.5; 7 pages; Oct. 4, 2010.

* cited by examiner

*Primary Examiner* — Jurie Yun
(74) *Attorney, Agent, or Firm* — Fitch, Even, Tabin & Flannery, LLP

(57) ABSTRACT

At least three radiation-detection views are used to facilitate identifying material as comprises an object being assessed along a beam path relative to that object. This comprises developing a first radiation-detection view (101) as corresponds to the material along the beam path, a second radiation-detection view (102) as corresponds to the material along substantially the beam path, and at least a third radiation-detection view (103) as corresponds to the material along substantially the beam path. At least one of the source spectra and detector spectral responses used for these radiation-detection views are different from one another for each view. One then uses (104) these radiation-detection views to identify the material by, at least in part, differentiating the material from other possible materials.

16 Claims, 6 Drawing Sheets

METHOD AND APPARATUS TO FACILITATE USING MULTIPLE RADIATION-DETECTION VIEWS TO DIFFERENTIATE ONE MATERIAL FROM ANOTHER

RELATED APPLICATION(S)

This application is related to co-pending and co-owned U.S. patent application Ser. No. 12/479,322, entitled METHOD AND APPARATUS TO FACILITATE USING FUSED IMAGES TO IDENTIFY MATERIALS and filed on even date herewith, which is incorporated by reference in its entirety herein.

TECHNICAL FIELD

This invention relates generally to the use of radiation-detection views to identify materials.

BACKGROUND

The capture of radiation-detection views of a given object using penetrating energy (such as X-rays or the like) is well known in the art. Such radiation-detection views often comprise images having areas that are relatively darker or lighter (or which otherwise contrast with respect to one another) as a function of the density, path length, and composition of the constituent materials that comprise the object being imaged. This, in turn, can serve to provide views of objects that are otherwise occluded from visual inspection.

The use of radiation-detection views finds myriad applications. In at least some application settings, however, merely ascertaining the presence or shape of an occluded object may be insufficient to address all attendant needs. In a security application setting, for example, objects that pose a serious security concern may share a same shape with other completely innocuous objects. In cases where the densities of such objects are similar, it can become impossible to discern from such data which constitutes a threat and which does not. A similar problem can occur when the density and path length product for two objects is substantially the same notwithstanding that they are formed of different materials. As a simple illustration in this regard, a four inch by four inch by three inch block of steel may look the same using one-dimensional radiography as a four inch by four inch by 1.75 inch block of lead notwithstanding that these two materials have considerably different densities.

It is also known in the art to employ two radiation-detection views of a same object formed using two different source-spectrum beams. In particular, one of the source-spectrum beams has a higher typical energy than the other. By comparing the differing energy attenuation information gleaned from such views, one can obtain additional information that relates to the composition of the object being viewed. In particular, the attenuation coefficients will vary with the utilized energy in a manner that depends on the chemical composition of the object.

Such a dual-energy approach can provide satisfactory results in some limited application settings. Generally speaking, when using relatively lower energies (as when the highest utilized energy does not exceed 1.022 MeV) the variation in attenuation results depends mainly upon differing coherent scattering, photoelectric behaviors, and Compton effects. At higher energies, however, the applicant notes that pair-production phenomena play an increasingly important role. In particular, pair production-influenced attenuation increases with increasing atomic number of the material being considered and increases with increasing photon energy while the attenuation due to other processes tends to either increase with increasing atomic number or remain substantially invariant to atomic number, but decreases with increasing photon energy. Therefore, for a given atomic number, there exists some energy (and this energy is above 1.022 MeV) where the attenuation stops decreasing with increasing energy and starts to increase, and the photon energy at which this change occurs is a function of atomic number.

In the dual-energy approach, one can in general glean information on the composition of an object by scanning with two different spectra and comparing the values measured using each spectrum. For example, using energies below 1.022 MeV, the ratio of low-energy transmission to high-energy transmission generally decreases with increasing atomic number, whereas using energies all above 10 MV, the ratio of low-energy transmission to high-energy transmission generally increases with increasing atomic number. For energies in between, generally the ratio of low-energy transmission to high-energy transmission increases with increasing atomic number up to a certain point, then the ratio begins to decrease with further increases to atomic number. Accordingly, a particular relatively high-Z material (such as Uranium) can have the same ratio as some lower-Z material. This leads to a corresponding ambiguity regarding the identity of the material. As a result, some materials cannot be reliably discriminated from one another when using high energies with only two spectra. Unfortunately, there are numerous application settings where high energies must be utilized.

BRIEF DESCRIPTION OF THE DRAWINGS

The above needs are at least partially met through provision of the method and apparatus to facilitate using multiple radiation-detection views to differentiate one material from another described in the following detailed description, particularly when studied in conjunction with the drawings, wherein.

Figure 1:
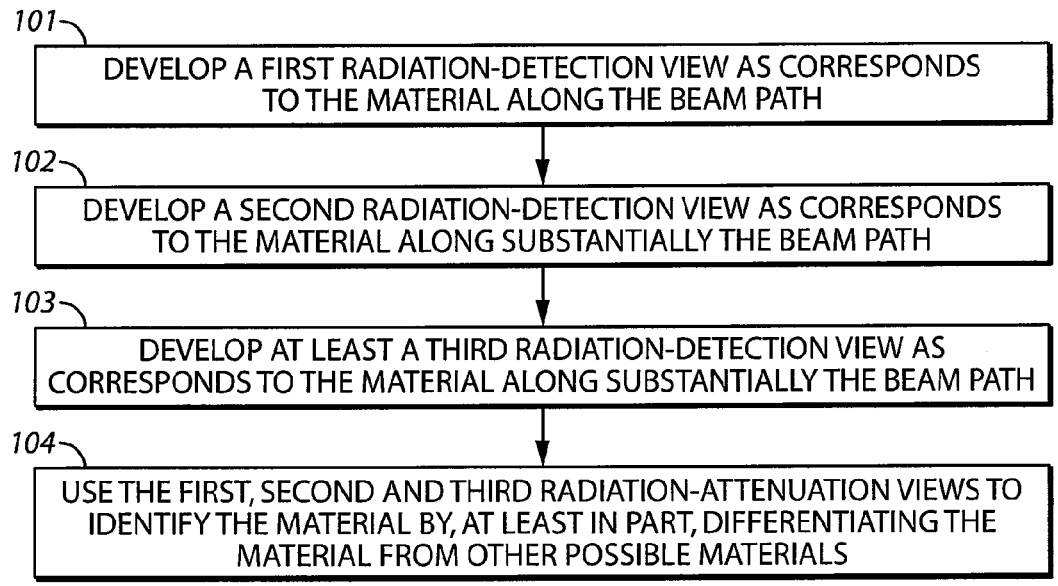
FIG. 1 comprises a flow diagram as configured in accordance with various embodiments of the invention.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, at least three radiation-detection views are used to facilitate identifying material as comprises an object being assessed along a beam path relative to that object. This comprises developing a first radiation-detection view as corresponds to the material along the beam path, a second radiation-detection view as corresponds to the material along substantially the beam path, and at least a third radiation-detection view as corresponds to the material along substantially the beam path. At least one of the source spectra and detector spectral responses used for these radiation-detection views are different from one another for each view. One then uses these radiation-detection views to identify the material by, at least in part, differentiating the material from other possible materials.

By one approach, this can comprise utilizing three different source-spectrum beams where at least one of the source spectra contains radiation above 1.022 MeV. This can comprise using three different sources for three different corresponding source-spectrum beams. By another approach this can comprise using at least one shared radiation source to yield at least two of the source-spectrum beams. For example, this can comprise using an interlaced radiation-spectrum source. As another example, a filter can be utilized with such a shared radiation source to yield the different source-spectrum beams.

By yet another approach, this can comprise utilizing a stacked detector to develop at least two of the radiation-detection views. Such a stacked detector can comprise, for example, at least two in-beam detectors. If desired, such in-beam detectors can both be comprised of the same material. In this case, the order of the materials will make the first detector (i.e., the detector that is closest to the source) more sensitive to lower-energy photons while the second detector is preferentially sensitive to higher-energy photons. By another approach, such a stacked detector can comprise at least two detectors that each comprise different conversion materials as compared to one another. By another approach, such a stacked detector can comprise at least two detectors that are formed of a same material but that are separated by a filter material that serves to filter beam spectrum between the first and second detector.

These various approaches can also be combined. For example, one can use a stacked detector with an interlaced source to provide a total of four detected spectra.

So configured, one can readily acquire three or more radiation-detection views using, at least in some cases, relatively high energy (where this reference to "relatively high energy" will be understood to refer to an energy that is higher than 1.022 MeV). The applicant has determined, in turn, that such a plurality of views will suffice in many instances to readily permit identification of a given material where prior art techniques would fail in these regards. Those skilled in the art will appreciate that these teachings are suitable for use in challenging application settings including numerous security and industrial settings where high energies are necessary and where it can be a mission requirement to reliably identify high atomic number materials.

These and other benefits may become clearer upon making a thorough review and study of the following detailed description. Referring now to the drawings, and in particular to FIG. 1, an illustrative process 100 that is compatible with many of these teachings will now be presented. In particular, this process 100 will serve to facilitate identifying material as comprises an object being assessed along a beam path (relative to the object). (As used herein, the expression "assessed" will be understood to refer to imaging-based processes but will also be understood to encompass other measurement-based processes that may not work directly with data that would ordinarily be characterized as an "image." It will also be understood that, for the sake of illustration in the following discussion and description, this beam path comprises ionizing radiation; those skilled in the art will recognize that other possibilities exist in these regards, however.)

This process 100 provides the step 101 of developing a first radiation-detection view as corresponds to the material along the beam path. This can comprise, for example, an X-ray-based image (such as a radiographic image) of the material that is built up from measurements along paths, each of which path has a corresponding viewing angle. By one approach, this first radiation-detection view can be formed using a first source-spectrum beam (such as, for example, a 3 MeV beam as is known in the art).

This process 100 also provides the step 102 of developing a second radiation-detection view as corresponds to the material along substantially the beam path. This can comprise, for example, another X-ray-based image of the material along a viewing angle that is substantially along the aforementioned beam path. By one approach, this second radiation-detection view can be formed using a second source-spectrum beam that is different from the first source-spectrum beam mentioned above (such as, for example, a 6 MeV beam as is known in the art).

Generally speaking, it may be preferred that both the second and the first radiation-detection views be formed along exactly the same beam path so that the two views essentially comprise a same point of view of the object. In some cases, this may not be possible nor is it necessarily an absolute requirement. Those skilled in the art will understand that the expression "substantially along the aforementioned beam path" is intended to encompass this notion that the second radiation-detection view should be based upon an orientation that is close, if not exactly the same, as the orientation used to develop the first radiation-detection view. The degree to which dissimilarity may be tolerated will of course depend upon the specifics of a given application setting. For some purposes it may be important to limit the dissimilarity to no more than one or two pixels. In other cases (for example, when employing software-based registration algorithms) a considerably higher degree of dissimilarity may be acceptable and tolerated.

As one illustrative example in these regards, consider two separate sources separated by 6 feet. For some view from the first source at time A, one can then use position encoder information (or velocity information) to choose a later time B when one should sample the second source so that the two resultant views correspond to the same point in the object. This can be done by choosing ahead of time when to sample the data (though such an approach may be susceptible to jitter) or by just sampling in some regular manner and then sorting out the results latter using, for example, a software-based approach.

This process 100 then also provides the step 103 of developing at least a third radiation-detection view as again corresponds to the material along (again) substantially the same beam path. And again, this can comprise another X-ray-based image of the material along a viewing angle that is again substantially along the aforementioned beam path. By one approach, this third radiation-detection view can be formed using a third source-spectrum beam that is different from the first and second source-spectrum beams mentioned above (such as, for example, a 9 MeV beam as is known in the art).

As noted above, different source-spectrum beams can be used when developing each of these radiation-detection views. This is not an essential requirement, however. Generally speaking, what is important is that at least one of the source spectra and the corresponding detector spectral responses used for these radiation-detection views are different from one another. (The applicant has identified a number of alternative ways by which one can meet this requirement. Numerous examples in these regards are provided below.)

This process 100 then accommodates the step 104 of using these first, second, and third radiation-detection views to identify the material of which the object is comprised by, at least in part, differentiating the material from other possible materials.

Figure 2:
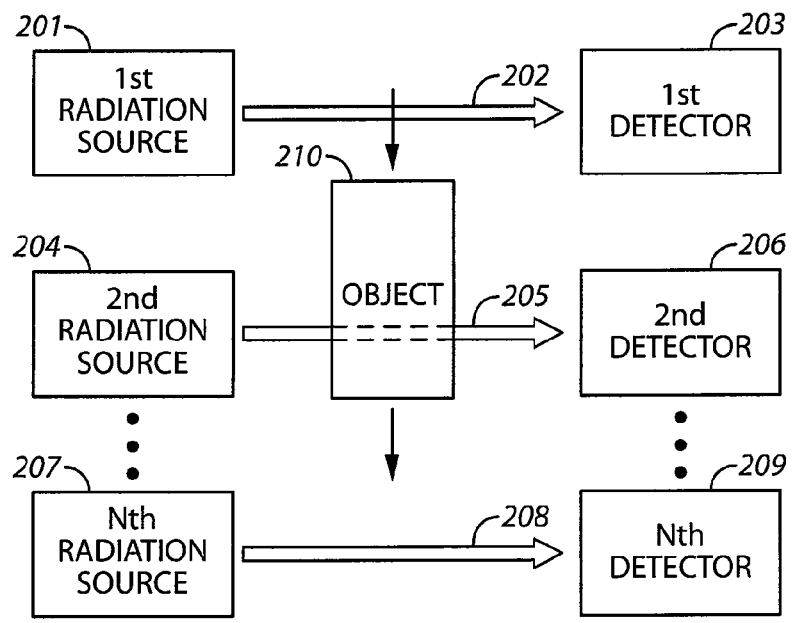
FIG. 2 comprises a block diagram as configured in accordance with various embodiments of the invention.

Referring now initially to FIG. 2, a number of alternative approaches to providing for the aforementioned development of these radiation-detection views using differing source spectra and/or detector spectral responses will now be provided. In this first example, a first through an Nth radiation source (201, 204, and 207, respectively, where "N" refers to an integer equal to or greater than "3") (also sometimes referred to herein as a "beam source") each provides a corresponding source-spectrum beam (202, 205, and 208, respectively) that differs from the other source-spectrum beams. At least one of these radiation sources provides a resultant source-spectrum beam that is greater than 1.022 MeV. As one illustrative example, and without intending any suggestion of limitations in these regards, the first radiation source 201 could comprise a 3 MeV source, the second radiation source 204 could comprise a 6 MeV source, and the third radiation source could comprise a 9 MeV source.

In the example just provided, there is a separate radiation source and a separate corresponding detector for each of the aforementioned first, second, and third (or more) radiation-detection views. In such a case, the object 210 being considered will be moved with respect to these sources/detectors (and/or one or more of the sources or detectors will be moved with respect to the object 210) in order to provide the necessary beam-path opportunities.

Figure 3:
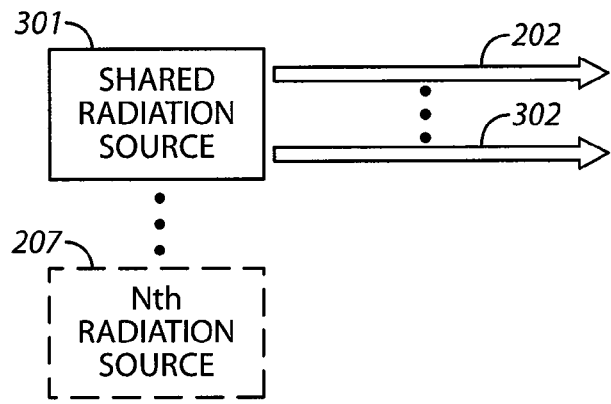
FIG. 3 comprises a block diagram as configured in accordance with various embodiments of the invention.

These teachings will accommodate other approaches in these regards, however. For example, and referring now to FIG. 3, a single shared radiation source 301 can provide two or more of the desired source-spectrum beams (202 and 302 in the illustrated example). By one approach this shared radiation source 301 can comprise an interlaced radiation spectrum source. Interlaced radiation spectrum sources are known in the art and require no further elaboration here. Such a shared radiation source 301 can serve to alternately provide, for example, 6 MeV source-spectrum beam and 9 MeV source-spectrum beam pulses.

Figure 4:
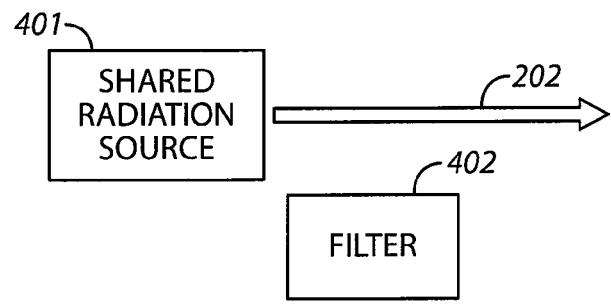
FIG. 4 comprises a block diagram as configured in accordance with various embodiments of the invention.
Figure 5:
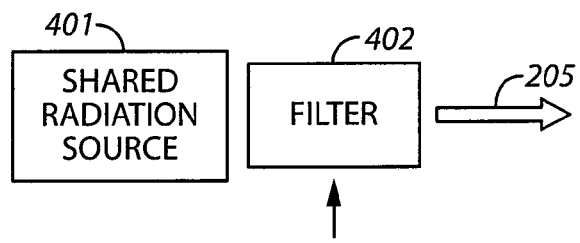
FIG. 5 comprises a block diagram as configured in accordance with various embodiments of the invention.

Referring now to FIGS. 4 and 5, and pursuant to another approach, a single shared radiation source 401 can be employed in conjunction with a moving filter 402 that can be rapidly moved in and out of the path of the source's radiation output. This filter 402 can be comprised of a material and have a thickness that absorbs some, but not all, of the beam's energy. In particular, the filter should absorb some energies preferentially more than others in order to effect a genuine change with respect to the resultant spectrum. By this approach (and by way of example), an unfiltered source-spectrum beam 202 (for example a nominal 9 MeV beam with no filter) can correspond to a beam with a lower typical energy while a filtered source-spectrum beam 205 (for example the same nominal 9 MeV beam, now with a 1" steel filter) can correspond to a beam with a higher typical energy. So configured, for example, one can use this shared radiation source 401 to develop a first one of the radiation-detection views without the filter 402 and then use this same shared radiation source 401 to develop a second one of the radiation-detection views by scanning the object with the filter 402 in place. So configured, moving the filter 402 rapidly in and out of the beam path will serve to rapidly change the source spectrum during a scan.

As yet another related approach in these regards, a plurality of different filters could be employed. One such filter could be comprised, for example, of lead while another such filter is comprised of a plastic material. Such an approach would give rise to up to four different source spectrums (unfiltered, using the lead filter alone, using the plastic filter alone, and using both the lead filter and the plastic filter at the same time). (Or, if desired, varying combinations of such materials can be utilized in a way that avoids the "unfiltered" option. For example, a rotatable wheel having a plastic section, a lead section, and a lead/plastic section could serve in these regards.)

Figure 6:
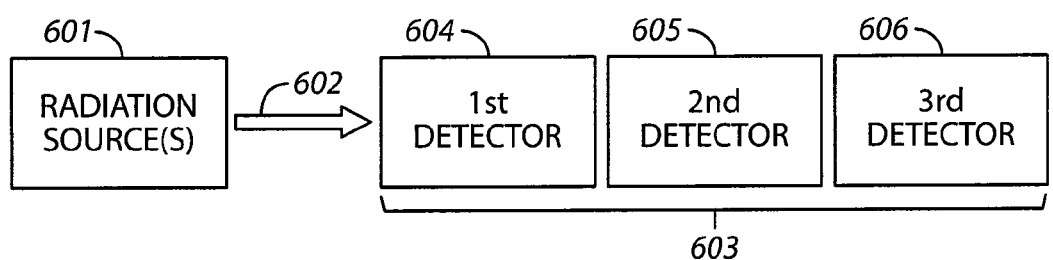
FIG. 6 comprises a block diagram as configured in accordance with various embodiments of the invention.

In the examples provided above, the different radiation-detection views are obtained by using differing source spectra. These teachings will also accommodate using differing detector spectral responses. To illustrate by way of a non-limiting example, and referring now to FIG. 6, this can comprise employing a stacked detector 603 in conjunction with one or more radiation sources 601. This stacked detector 603 can have two or more in-beam detectors. This illustrative example depicts three in-beam detectors 604-606. So configured, the source-spectra beam 602 emitted by the radiation source 601 will be directed through each of the first, second, and third in-beam detectors 604-606 in turn.

So configured, for example, one can develop the aforementioned first radiation-detection view by detecting the source-spectrum beam 602 using the first detector 604 as comprises a part of this stacked detector 603. One can then also develop the aforementioned second radiation-detection view by detecting this source-spectrum beam 602 using the second detector 605 as also comprises a part of this stacked detector 603.

In the illustrated example, the third radiation-detection view can be developed by detecting the same source-spectrum beam 602 by using the third detector 606 as comprises a part of this stacked detector 603. Alternatively, if desired, the radiation source 601 can comprise a shared radiation source as described above. In this case, when switching to a source-spectrum beam 602 having a different source spectrum source potential, the third radiation-detection view can be developed by detecting this subsequent source-spectrum beam 602 by again using the first detector 604. Those skilled in the art will understand that a fourth radiation-detection view can be developed in this case by detecting this subsequent source-spectrum beam 602 by again using the second detector 604 as well. (Those skilled in the art will recognize that the aforementioned reference to a different source spectrum may be viewed broadly enough to encompass the concepts of different nominal energy or different end point energy depending upon the particular application setting.)

By one approach, the first detector 604 can comprise a first conversion material that is comprised of a first material while the second detector 605 comprises a second conversion material that is comprised of the same type of material, placed substantially in line with the first detector. Typically, the first detector would be shorter (in a stopping direction) than the second detector (for example, the first detector 604 might be 4 mm $CdWO_4$ and the second detector 605 might be 26 mm $CdWO_4$). By this approach, this first detector 604 will act as a filter for the second detector 605, so the two detectors effectively see different source spectra. By another approach, the second detector can be comprised of a second material different than the first material, again placed substantially in line with the first detector. This could accentuate the difference between the two detectors. (As used herein, it will be understood that the expression "conversion material" can refer to a scintillator (such as cadmium tungstate or bismuth germinate), a direct-conversion material (such as amorphous silicon or cadmium zinc telluride), or a suitable gas (such as xenon). Such conversion materials are known in the art and require no further elaboration here.)

By another approach, the first detector 604 can comprise a first conversion material that is comprised of a first material while the second detector 605 comprises a second conversion material that is comprised of a second material that is different than the first material (where the two detectors are not necessarily in line with each other). By this approach, these two detectors 604 and 605 will exhibit differing detector spectral responses. These differing detector spectral responses, in turn, are readily employed to develop the aforementioned differing radiation-detection views.

By another approach, the first radiation-detection view can be developed using the first detector 604 where the first detector 604 comprises one output from a photon-counting detector, and the second radiation-detection view can be developed using the second detector 605 where the second detector 605 comprises an energy-integrating detector. By another approach, the first radiation-detection view can be developed using the first detector 604 where the first detector 604 comprises one output from an energy-discriminating photon-counting detector, the second radiation-detection view can be developed using the second detector 605 where the second detector 605 comprises a second output from an energy-discriminating photon-counting detector, and the third radiation-detection view can be developed using the third detector 606 where the third detector 606 comprises an energy-integrating detector.

By yet another approach, the first radiation-detection view can be developed using the first detector 604 where the first detector 604 comprises one output from an energy-discriminating photon-counting detector, the second radiation-detection view can be developed using the second detector 605 where the second detector 605 comprises a second output from an energy-discriminating photon-counting detector, and the third radiation-detection view can be developed using the third detector 606 where the third detector 606 comprises a third output from an energy-discriminating photon-counting detector. (When using a photon counting (or energy-discriminating photon-counting) detector in conjunction with an energy-integrating detector, they might share the same piece of conversion material, or they might each have their own conversion material.) These various detector types are known in the art and require no further description here. In this case, the differing detector spectral responses can again be leveraged to provide these differing views of the object along a substantially common beam path.

Figure 7:
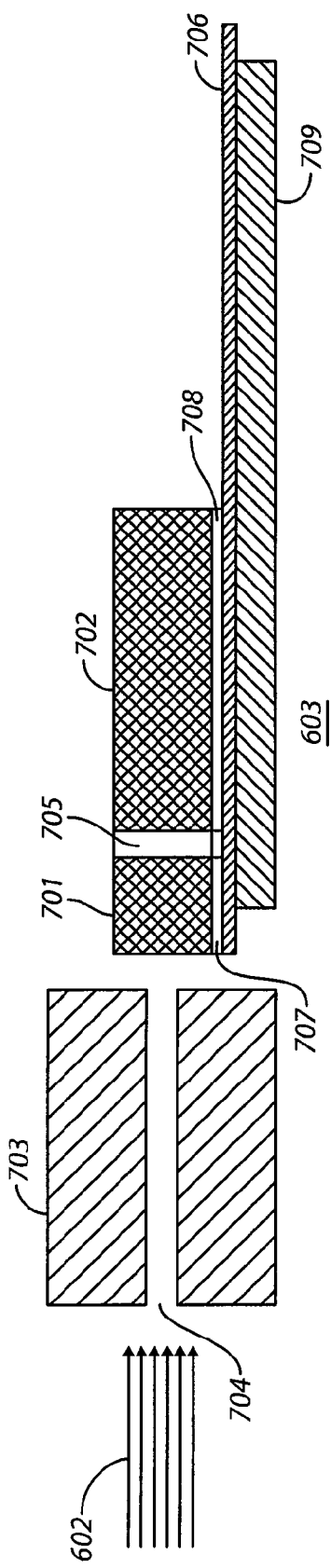
FIG. 7 comprises a side-elevational schematic view as configured in accordance with various embodiments of the invention.
Figure 8:
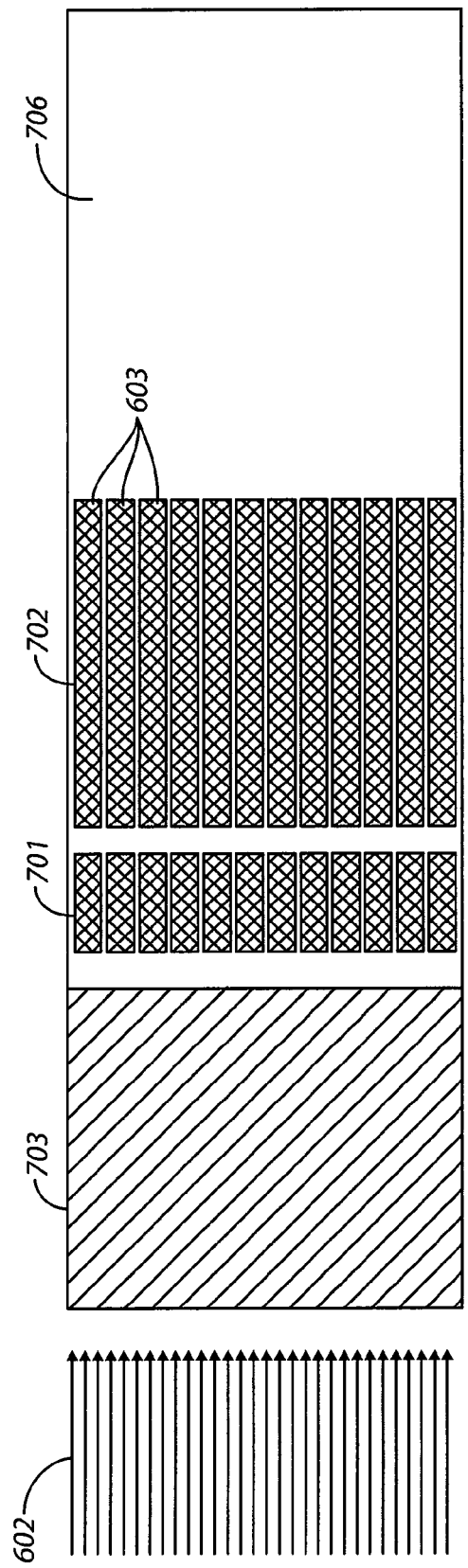
FIG. 8 comprises a top plan schematic view as configured in accordance with various embodiments of the invention.

The applicant has determined that certain challenges present themselves when using a stacked-detector approach. Some further description in these regards is therefore warranted. Referring now to FIGS. 7 and 8, an array of stacked detectors 603 can comprise, in this example, a plurality of side-by-side stacked detectors 603 that each comprise a front scintillator 701 and a back scintillator 702. A pair of blades 703 serve as a collimator and define an entrance aperture 704 for the stacked detector 603. These blades 703 are formed of a highly absorbent material such as tungsten.

In this example, for many typical scintillator materials and energy ranges, the front scintillator 701 will have a relatively stronger response to lower-energy photons that will tend to stop before reaching the back scintillator 702. Conversely, the back scintillator 702 will have a relatively stronger response to higher-energy photons that will tend to pass through the front scintillator 701. If desired, the materials selected to comprise these scintillators can be such as to enhance these characteristic responses. Those skilled in the art will recognize that other circumstances may lead to alternative results.

The illustrated stacked detector 603 also has a block 705 disposed between the two scintillators 701 and 702. This block 705 can comprise a non-scintillating absorbing material (such as, but not limited to, steel, aluminum, or tungsten) that serves as a filter to thereby further shape the spectrum (generally by reducing the number of lower-energy X-ray photons that reach the back scintillator 702). When providing a plurality of side-by-side stacked detectors as shown in FIG. 8, these teachings will also readily accommodate providing additional blocking material between adjacent stacked detectors in order to reduce crosstalk between adjacent detectors.

A circuit substrate 706 supports the aforementioned scintillators 701 and 702 along with their corresponding photodetectors 707 and 708 and processing circuitry 709. In this illustrative embodiment, these non-scintillator components are disposed behind the aforementioned blades 703. This orientation, in turn, protects the photodetectors 707 and 708 and the processing circuitry 709 from direct exposure to the incoming radiation. This protection can lead to an extended service life for such components as such radiation can alter or damage the functionality of such components.

Figure 9:
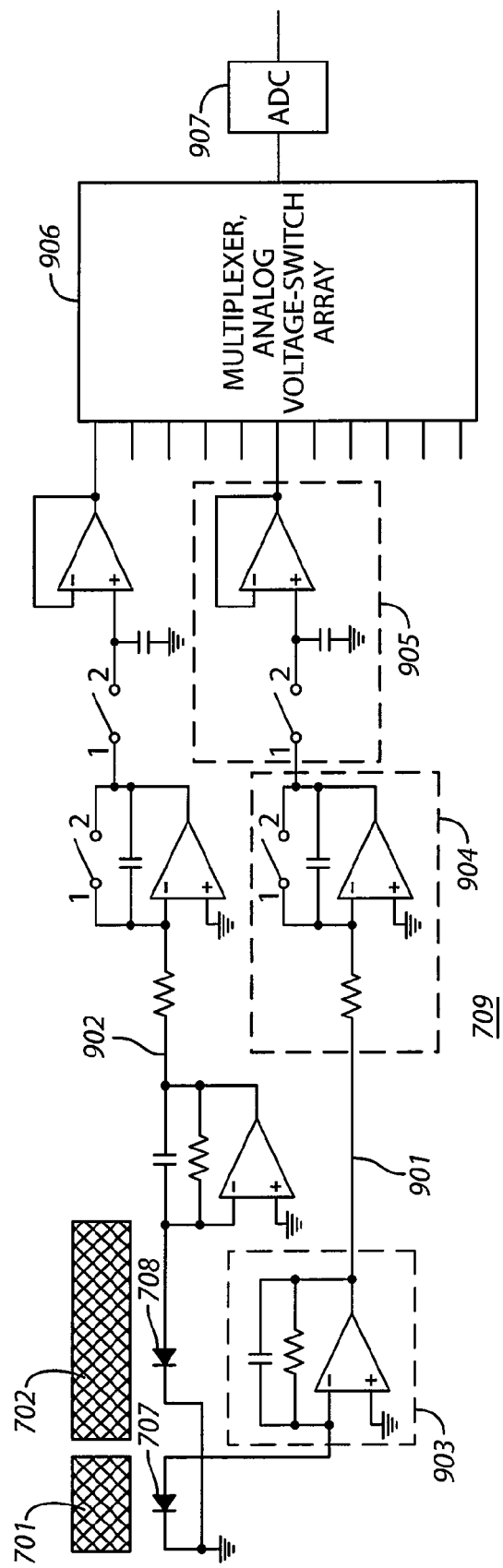
FIG. 9 comprises a schematic view as configured in accordance with various embodiments of the invention.

Referring now to FIG. 9, a first approach for the processing circuitry 709 will be described. In this example there are two identical processing chains 901 and 902 (one for each photodiode 707 and 708, respectively). As they are identical, only one will be described in detail.

The processing chain 901 comprises a trans-resistance preamplifier stage 903 that provides a voltage as corresponds to current through the photodiode 707 to an integration stage 904. This integration stage 904 includes a reset switch. So configured, this integration stage 904 provides an output voltage that is proportional to a time integral of the input voltage from the trans-resistance preamplifier stage 903 over a given time period when the reset switch is open.

The output of the integration stage 904 in turn couples to a track/hold circuit 905. The track/hold circuit 905 includes a switch that opens shortly before the integration stage 904 switch resets. The track/hold circuit 905 also includes a hold capacitor that maintains a constant voltage at a buffer input while the integration stage 904 acquires a next sample. The outputs of the track/hold circuits for all of the processing chains connect to an analog-to-digital converter 907 via an intervening multiplexer 906.

Figure 10:
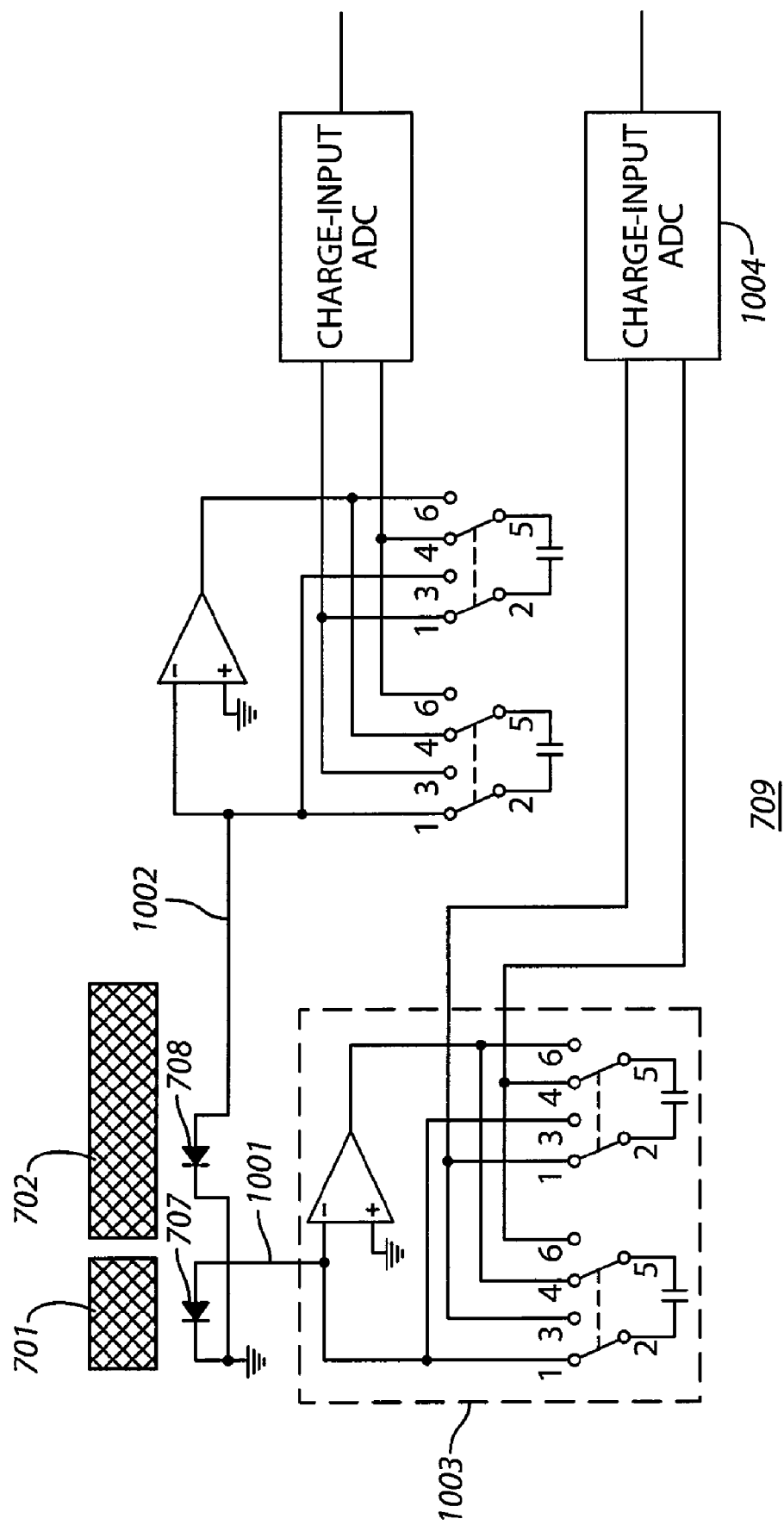
FIG. 10 comprises a schematic view as configured in accordance with various embodiments of the invention.

Referring now to FIG. 10, a second approach for the processing circuitry 709 will be described. In this example there are again two identical processing chains 1001 and 1002. And again, for the sake of brevity, only one of these chains 1001 will be described in detail.

In this approach, the current from the photodiode 707 feeds directly into an integration stage 1003. This integration stage 1003 includes a commutating switch that alternately connects one capacitor (of a matched pair of capacitors) to a feedback path for an integrating amplifier. So configured, the photodiode charge accumulates on that one capacitor while the other capacitor is connected to a charge-sensitive analog-to-digital converter 1004. The latter discharges the latter capacitor during the digitization process before that capacitor is then again reconnected to the integrating amplifier.

When using the first approach described above, care may be necessary when also using an interlaced-energy pulsed radiation source. This is because any signal remaining at the output of the preamplifier stage (due, for example, to finite speed and recovery time of the input circuit) at the end of a given sample can contribute to the signal that is integrated during a following sample. Such concerns are mitigated when employing the second described approach. This is because the two energy states associated with the source are directed to different capacitors (presuming that the commutation switch connects the two capacitors in an alternation pattern that matches the alternation pattern of the interlaced source). Using separate capacitors essentially eliminates any hangover between the states corresponding to each capacitor as any charge remaining on one capacitor after digitization will affect only the next sample at the same energy state (presuming one capacitor per state).

Figure 11:
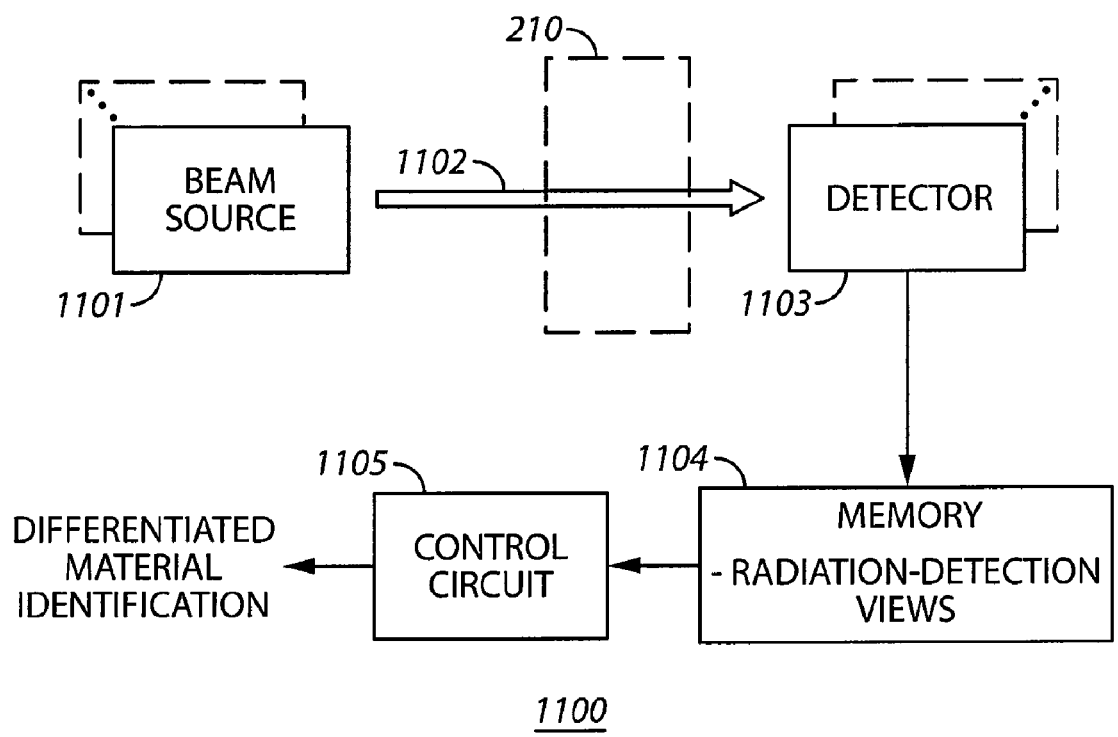
FIG. 11 comprises a block diagram as configured in accordance with various embodiments of the invention.

Referring now to FIG. 11, by one illustrative approach these teachings can be employed to provide an apparatus 1100 that can facilitate identifying material as comprises an object 210 being assessed along a beam path 1102 relative to the object 210. This apparatus 1100 can comprise at least one beam source 1102 that is configured to provide this beam path 1102 and at least one detector 1103 disposed along this beam path 1102. This beam source 1101 and detector 1103 can comprise, for example, any configuration as has been described herein. As described herein, these components are used to provide varying source spectra and/or detector spectral responses in order to develop at least first, second, and third radiation-detection views as correspond to the object 210 along the beam path 1102.

This apparatus 1100 can further comprise a memory 1104 that couples to receive and store the radiation-detection views as correspond to the material along the beam path 1102 as described above. A control circuit 1105 can operably couple in turn to the memory 1104. This control circuit can comprise a fixed-purpose hard-wired platform or can comprise a partially or wholly programmable platform. All of these architectural options are well known and understood in the art and require no further description here.

This control circuit 1105 can be configured (using, for example, programming as will be well understood by those skilled in the art) to use these radiation-detection views to identify the material that comprises the object 210 by, at least in part, differentiating the material from other possible materials.

Those skilled in the art will know that present dual-energy material discrimination approaches generally work by establishing a relationship between ordered pairs of data and the corresponding material, and applying this relationship to determine the material of unknown objects (or at least glean characterizing information regarding the material of unknown objects). For example, establishing the relationship may comprise theoretical calculations, or it may comprise calibration, where one measures the high-energy attenuation and the low-energy attenuation through different materials and thicknesses to calibrate the system's response to different materials. The two elements of the ordered pairs can be, for example, high-energy transmission and low-energy transmission, or they can be high-energy transmission and the ratio of high-energy transmission to low-energy transmission. These basic approaches can be readily extended to more dimensions to accommodate the increased information made available pursuant to these teachings. This can comprise, for example, replacing the ordered pairs of the prior art approach with triples or quadruples (and so forth) in this higher-dimension vector space. See, for example, the teachings set forth in the aforementioned METHOD AND APPARATUS TO FACILITATE USING FUSED IMAGES TO IDENTIFY MATERIALS.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate identifying material as comprises an object being assessed along a beam path, relative to the object, comprising:
    developing a first radiation-detection view as corresponds to the material along the beam path using a first interlaced-energy x-ray pulse and a first detector of a stacked detector;
    developing a second radiation-detection view as corresponds to the material along substantially the beam path using the first interlaced-energy x-ray pulse and a second detector of the stacked detector, wherein the second detector has a different spectral response than the first detector;
    developing at least a third radiation-detection view as corresponds to the material along substantially the beam path using a second interlaced-energy x-ray pulse and the first detector of the stacked detector, wherein the second interlaced-energy x-ray pulse has a different source spectra as compared to the first interlaced-energy x-ray pulse and wherein additional radiation-detection views may be developed but without using additional interlaced-energy x-ray pulses having a different source spectra as compared to the first and second interlaced-energy x-ray pulses;
    using the first, second, and third radiation-detection views to identify the material by, at least in part, differentiating the material from other possible materials.

2. The method of claim 1 wherein the stacked detector comprises a stacked detector having at least two in-beam detectors.

3. The method of claim 1 wherein the stacked detector comprises a stacked detector having photo-sensitive detectors that are protected from the beam path.

4. The method of claim 3 wherein the stacked detector having photo-sensitive detectors that are protected from the beam path comprises a stacked detector having photo-sensitive detectors that are disposed external to the beam path.

5. The method of claim 1 wherein the stacked detector comprises a stacked detector comprised of at least two detectors each having different conversion materials as compared to one another.

6. The method of claim 1 wherein the stacked detector comprises a stacked detector having a first scintillator that is functionally separated from a second scintillator by non-scintillating material, where the non-scintillating material acts to filter beam spectrum between the first and second scintillators.

7. The method of claim 1 further comprising:
using multiple-channel electronics to process corresponding detector signals to thereby reduce crosstalk between radiation-detection views separated in time.

8. The method of claim 1 wherein the stacked detector comprises a stacked detector having a first scintillator and a second scintillator that are comprised of substantially identical materials.

9. The method of claim 1 wherein the stacked detector comprises a stacked detector having a first scintillator that is comprised of a first material and a second scintillator that is comprised of a second material, wherein the first material is different from the second material.

10. An apparatus to facilitate identifying material as comprises an object being assessed along a beam path, relative to the object, comprising:
an interlaced-energy pulsed x-ray beam source configured to provide first and second interlaced-energy x-ray pulses having different source spectra from one another along the beam path;
a stacked detector comprising a first and second detector disposed along the beam path, wherein the first and second detector have a different spectral response from one another;
a memory having stored therein information regarding:
a first radiation-detection view as corresponds to the material along the beam path formed using the first interlaced-energy x-ray pulse from the interlaced-energy pulsed x-ray beam source and the first detector of the stacked detector;
a second radiation-detection view as corresponds to the material along substantially the beam path formed using the first interlaced-energy x-ray pulse from the interlaced-energy pulsed x-ray beam source and the second detector of the stacked detector;
at least a third radiation-detection view as corresponds to the material along substantially the beam path formed using the second interlaced-energy x-ray pulse from the interlaced-energy pulsed x-ray beam source and the first detector of the stacked detector, wherein additional radiation-detection views may be included but wherein the additional radiation-detection views are not formed using other than one of the first and second interlaced-energy x-ray pulses;
a control circuit operably coupled to the memory and being configured to use the first, second, and third radiation detection views to identify the material by, at least in part, differentiating the material from other possible materials.

11. The apparatus of claim 10 wherein the stacked detector comprises a stacked detector having photo-sensitive detectors that are protected from the beam path.

12. The apparatus of claim 11 wherein the stacked detector having photo-sensitive detectors that are protected from the beam path comprises a stacked detector having photo-sensitive detectors that are disposed external to the beam path.

13. The apparatus of claim 10 wherein the stacked detector comprises a stacked detector comprised of at least two detectors each having different conversion materials as compared to one another.

14. The apparatus of claim 10 wherein the stacked detector comprises a stacked detector having a first scintillator that is functionally separated from a second scintillator by non-scintillating material, where the non-scintillating material acts to filter beam spectrum between the first and second scintillators.

15. The apparatus of claim 10 wherein the stacked detector comprises a stacked detector having a first scintillator and a second scintillator that are comprised of substantially identical materials.

16. The apparatus of claim 10 wherein the stacked detector comprises a stacked detector having a first scintillator that is comprised of a first material and a second scintillator that is comprised of a second material, wherein the first material is different from the second material.

* * * * *